US 9,922,384 B2

(12) United States Patent
Cobb et al.

(10) Patent No.: US 9,922,384 B2
(45) Date of Patent: Mar. 20, 2018

(54) PHARMACEUTICAL WILL CALL SYSTEM AND METHOD

(76) Inventors: William Robert Cobb, Spartanburg, SC (US); Chris Gregory Cox, Columbus, NC (US); Barton Carter Mitchell, Pauline, SC (US); Derek William Thompson, Knightdale, NC (US); Brian Marshall Burney, Wake Forest, NC (US)

( * ) Notice: Subject to any disclaimer, the term of this patent is extended or adjusted under 35 U.S.C. 154(b) by 1262 days.

(21) Appl. No.: 13/462,374

(22) Filed: May 2, 2012

(65) Prior Publication Data

US 2013/0297325 A1 Nov. 7, 2013

(51) Int. Cl.
| G06Q 10/00 | (2012.01) |
| G06Q 50/00 | (2012.01) |
| G06Q 50/22 | (2018.01) |
| G06Q 10/10 | (2012.01) |
| G06Q 30/06 | (2012.01) |

(52) U.S. Cl.
CPC ............ *G06Q 50/22* (2013.01); *G06Q 10/10* (2013.01); *G06Q 30/06* (2013.01)

(58) Field of Classification Search
USPC ........................................................ 705/2, 3
See application file for complete search history.

(56) References Cited

U.S. PATENT DOCUMENTS

| 5,962,834 A | 10/1999 | Markman |
| 6,520,544 B1 | 2/2003 | Mitchell et al. |
| 6,677,852 B1 | 1/2004 | Landt |
| 6,830,181 B1 | 12/2004 | Bennett |
| 7,109,864 B2 | 9/2006 | Maloney |
| 7,218,231 B2 | 5/2007 | Higham |
| 7,317,393 B2 | 1/2008 | Maloney |
| 7,448,544 B1 | 11/2008 | Louie et al. |
| 7,496,521 B1 | 2/2009 | Louie et al. |
| 7,537,155 B2 | 5/2009 | Denenberg et al. |
| 7,554,449 B2 | 6/2009 | Highham |
| 7,887,146 B1 | 2/2011 | Louie et al. |
| 7,938,326 B2 | 5/2011 | Dearing et al. |
| 7,982,623 B2 | 7/2011 | Higashionji et al. |
| 8,006,903 B2 | 8/2011 | Braun et al. |
| 8,009,017 B2 | 8/2011 | Park et al. |
| 8,025,228 B2 | 9/2011 | Dearing et al. |
| 8,090,632 B1 | 1/2012 | Ortiz et al. |
| 8,094,028 B2 | 1/2012 | Braun et al. |
| 8,113,424 B2 | 2/2012 | Philippe |
| 2003/0067381 A1* | 4/2003 | Mitchell et al. ............. 340/5.92 |

(Continued)

*Primary Examiner* — Sean K. Hunter
(74) *Attorney, Agent, or Firm* — Southeast IP Group, LLC.; Thomas L. Moses

(57) ABSTRACT

A wireless computerized will call system is provided for filling prescriptions and then locating specific prescriptions that have been filled when the customer arrives to pick up the prescription. The system includes a computer workstation or network, a wireless transmitter, and hanger bags for temporarily storing prescriptions awaiting customer pick up. The hanger bags are equipped with wireless receivers and transducers. When a pharmacy worker commands the computer system to locate a specific prescription, the specific hanger bag containing that prescription receives a wireless signal from the computer system and activates the transducer on the hanger bag to alert the pharmacy worker to the location of the prescription.

14 Claims, 3 Drawing Sheets

(56) References Cited

U.S. PATENT DOCUMENTS

| | | |
|---|---|---|
| 2003/0093295 A1* | 5/2003 | Lilly et al. .................. 705/2 |
| 2004/0256452 A1 | 12/2004 | Coughlin et al. |
| 2008/0059228 A1 | 3/2008 | Bossi et al. |
| 2008/0162188 A1 | 7/2008 | Kripalani et al. |
| 2008/0303638 A1 | 12/2008 | Nguyen et al. |
| 2009/0187424 A1 | 7/2009 | Grabowski |
| 2010/0036678 A1 | 2/2010 | Bray |
| 2010/0042437 A1 | 2/2010 | Levy et al. |
| 2010/0185458 A1 | 7/2010 | Newcomb et al. |
| 2011/0068922 A1 | 3/2011 | Ross |
| 2011/0090065 A1 | 4/2011 | Overhultz et al. |
| 2011/0166878 A1 | 7/2011 | Louie et al. |
| 2011/0184751 A1 | 7/2011 | Holmes |
| 2011/0285506 A1 | 11/2011 | Hillis |
| 2011/0291834 A1 | 12/2011 | Boldyrev et al. |
| 2012/0062366 A1 | 3/2012 | Pappu et al. |

\* cited by examiner

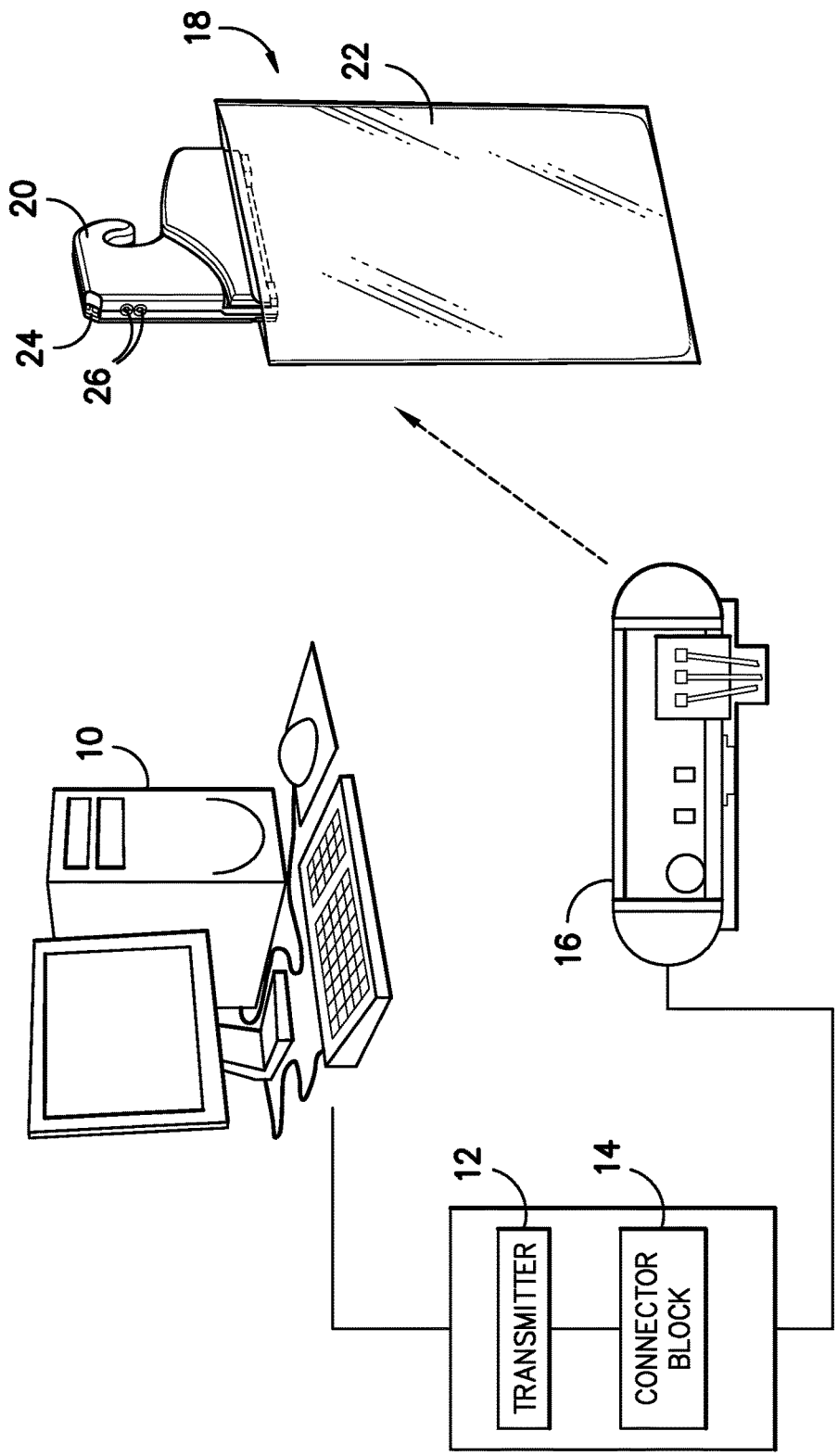
FIG. -1-

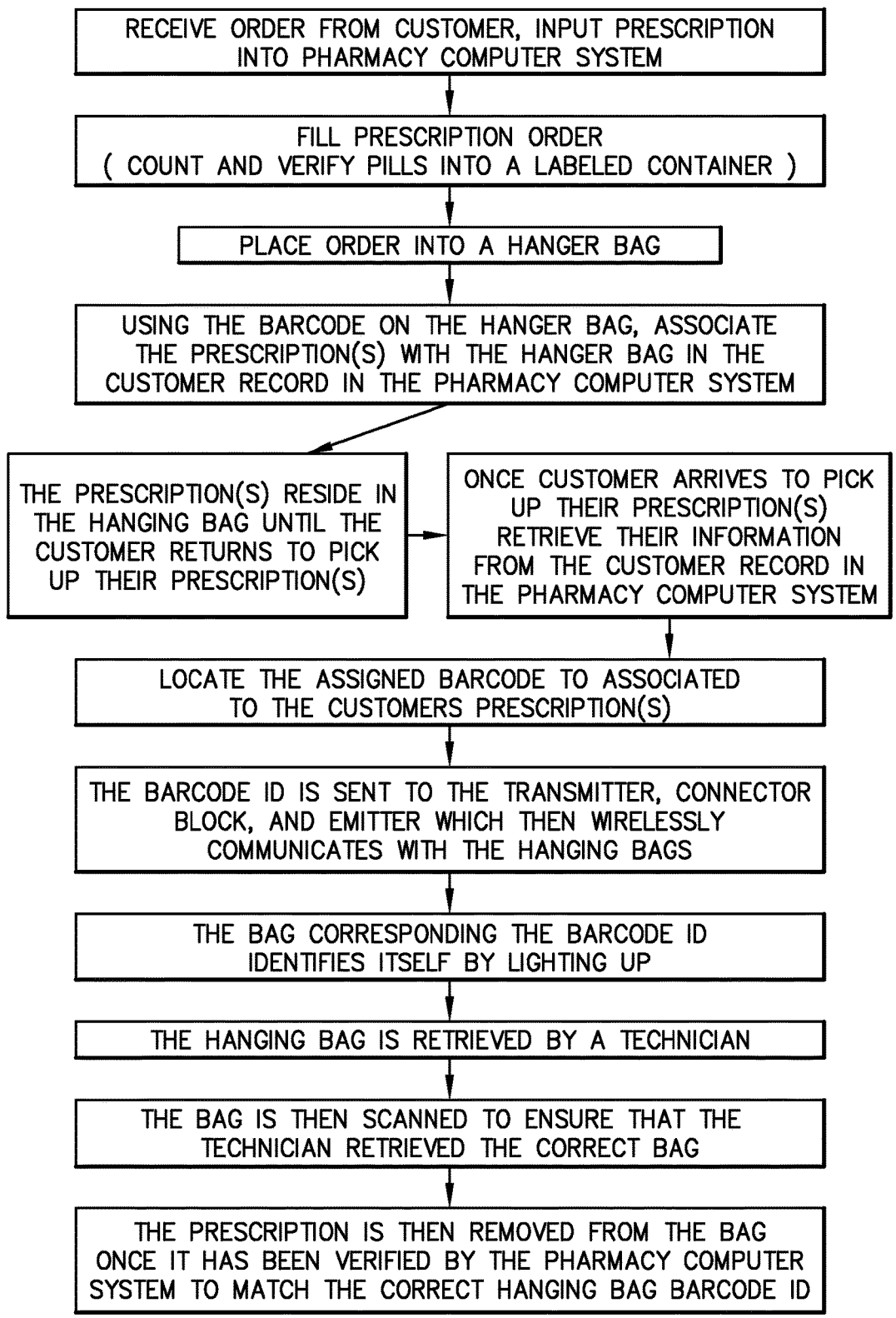
FIG. -2-

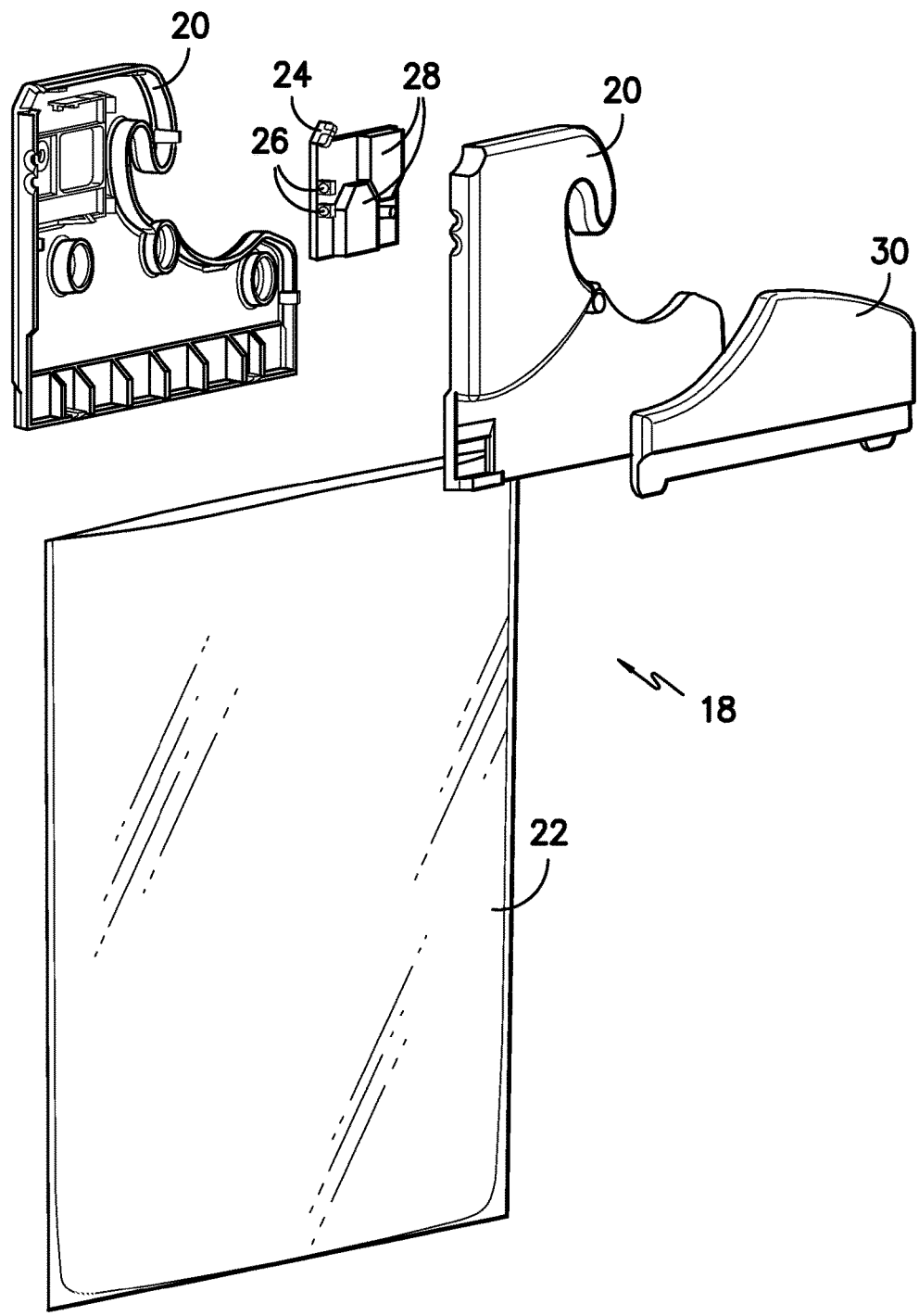
FIG. —3—

PHARMACEUTICAL WILL CALL SYSTEM AND METHOD

BACKGROUND OF THE INVENTION

The present invention relates generally to systems for locating items within a defined area. More specifically, the present invention includes a wireless computerized system for filling prescriptions, and then locating specific prescriptions that have been filled when the customer arrives to pick up the prescription.

There are several systems available today for locating and keeping track of various types of items, and prescription medications in particular. U.S. Pat. No. 7,448,544 is directed to a pharmacy prescription order identification system that permits individual detection and tracking of prescription orders even when they are all contained within a bulk container. Each prescription order in the bulk container has a uniquely identified tag. The tag is uniquely coded such that a tag reader can substantially simultaneously read a plurality of tags, thereby facilitating bulk processing and tracking of prescription orders. In a preferred embodiment the computer system compares the detected prescription orders in a bulk shipment with a provided manifest and alerts a worker of any discrepancies found.

U.S. Pat. No. 7,537,155 discloses a will call system for automating the management of storage and retrieval of items, preferably medical prescriptions. The automated system provides informational control of all items in the system. The automated will call monitors the length of time an item remains in the system, and into which location an item is placed. An article sensor provides absolute confirmation that an item has been placed or removed from a designated location in the storage units. The automated will call system uses a controller to permit users to monitor and optimize the storage and retrieval procedures.

U.S. Pat. No. 7,887,146 describes a storage system for a pharmacy that has a frame containing a rack-like structure with a plurality of storage carriers detachably suspended therefrom. The carriers are sized to receive filled prescription orders and the like and include individual identifiers that facilitate locating the carriers at a specific location on the rack-like structure. Preferably, the storage system includes a tracking system that detects, monitors, and displays to a worker the location of the storage carrier containing a particular customer's prescription order, thereby providing easy retrieval of the customer's prescription order.

U.S. Pat. No. 7,496,521 is directed to a pharmacy prescription order identification system that has a uniquely identified tag that travels with the prescription order throughout the pharmacy and is wirelessly connected to a computer system. The tag includes one or more worker signaling devices, such as lights or an audio speaker, that activate in response to either input from the pharmacy worker or other predetermined criteria to identify the prescription order to the pharmacy worker. In a preferred embodiment, the tag includes a plurality of worker signaling devices, and the activation of each transducer alerts a pharmacy worker to a different status of the prescription order. More preferably, the prescription order identification system includes a computer system that allows a pharmacy worker to individually access a customer's record, then activate the worker signaling devices on the tag associated with that customer's prescription order, thereby allowing a particular prescription order within the pharmacy to be easily identified. In addition, the computer system can automatically monitor the status of all pending prescription orders within the pharmacy and using predefined criteria, such as the elapsed time the prescription order has been within the pharmacy, automatically activate the worker signaling devices on the tags associated with the particular prescription orders meeting that criteria.

U.S. Pat. No. 8,006,903 describes an apparatus that includes a processor configured to operate a software application, which is configured to receive selection of a number of discrete groups into which to divide a plurality of identified products. The products are located at respective storage locations in a collection of storage locations. The software application is therefore configured to divide the identified products into discrete groups such that the areas of the resulting groups of products at respective storage locations are substantially non-overlapping. The software application is further configured to assign the groups of products to respective workstation computers, each of which is configured to generate and transmit, for each of one or more of the products of a respective group, a signal to an associated RFID tag to thereby direct the RFID tag to generate a notification signal. A method and computer program product for managing inventory are also provided.

U.S. Pat. No. 6,830,181 discloses a system and method which utilizes a dual function reader device, which may be a hand-held inventory control device, which first performs an optical read of an optical bar code on a carrier unit, then based on the identification of other information obtained from the optical read a RF read is made of a RF tag attached to, or within, the carrier unit. An indicator light on the carrier unit illuminates when the optical read is completed, which allows an operator to visually verify that the optical read has transpired for the desired carrier unit. The RF tag provides data regarding the inventory of the goods stored within, or on, the carrier unit, the temperature of the goods, the shelf-life of the goods, the source and/or destination of the carrier unit and/or the goods, or other information. Data can also be written to the RF tag by the reader.

However, many of the above referenced systems suffer from serious disadvantages, including high cost, difficulty of installation, unnecessary complexity, and difficulty of use. Thus, it would be desirable to provide a simple, low-cost, computerized will-call system and method for filling, locating and keeping track of prescription orders.

SUMMARY OF THE INVENTION

A system for use in a pharmacy includes a computer work station or server, a transmitter, a connector block (signal booster/amplifier), at least one infrared (IR) emitter, and a number of hangers attached to clear plastic bags. Each hanger includes a bag, an IR receiver and two LED lights, one red and one green, as well as a bar code and a chip that is programmed to match the barcode. All of the components are connected by cable, which transmit communications and power, except for the hanger, which is battery operated.

In use, the system provides an easy and convenient method for filling prescriptions and refills at pharmacies and the like. For example, a customer calls in a prescription, and the pharmacist begins the process of filling the prescription by entering the customer and pharmaceutical information into the pharmacy management software. The prescription is processed, so that the proper pills are counted and placed into a container, and a label is applied to the container. Then, the prescription is placed into a hanger bag, and the barcode for the bag is scanned into the system to match the prescription information with the specific hanger bag. Next, the hanger bag is placed on a rack.

When the customer arrives at the pharmacy to pick up the prescription, the pharmacist accesses the computer work station, scans his security card, which matches the pharmacist with the prescription order in the computer system, selects the customer record, and accesses the request for pickup or checkout of the prescription(s). The system sends a command through the transmitter, the connector block, and on to the IR emitter, which wirelessly broadcasts the signal to the hanger rack. The signal is unique to the particular hanger bag. When the signal is wirelessly broadcast by the IR emitter, it is received by each of the IR receivers within all of the hanger bags. The target hanger bag with the customer's prescription illuminates the light or lights attached to the hanger, so that the pharmacist can easily find the target hanger bag. All other hanger bags simply ignore the signal, because the signal is unique to that particular hanger bag, due to the programmed chip and barcode attached to that specific hanger bag. Once the target bag is retrieved by the pharmacist, he or she brings the bag and prescription(s) back to the computer work station and scans the barcode from the hanger bag, in order to ensure that the proper bag and prescription were retrieved for that specific order. Then, the prescription(s) in the bag are released to the customer, who signs a receipt.

BRIEF DESCRIPTION OF THE DRAWINGS

These and other features, aspects, and advantages of the present invention will become better understood with regard to the following description, appended claims, and accompanying drawings where:

FIG. 1 schematically illustrates the components of the pharmaceutical will call system;

FIG. 2 is a flow-chart diagram illustrating the steps of the pharmaceutical will call system; and FIG. 3 is a perspective exploded view of one embodiment of a hanger bag, illustrating the components positioned therein.

DETAILED DESCRIPTION OF THE INVENTION

A first embodiment of the pharmaceutical will call system is shown in FIGS. 1-3. In a preferred embodiment, the system includes a computer work station 10 and/or server, a transmitter 12, a connector block 14 (signal booster/amplifier), at least one infrared (IR) emitter 16, and a number of hanger bags 18, each including a hanger portion 20 attached to clear plastic bag 22. Each hanger bag 18 may include a bag 22 (preferably clear plastic), an IR receiver 24 a transducer (preferably two LED lights 26, one red and one green), and batteries 28, as well as a bar code and a chip that is programmed to match the barcode. The hanger bag 18 may also include a snap-fit latch 30, which is attached to one side of the bag, and allows the bag to be opened and snapped into a closed position. All of the components are connected by cable, which transmit communications and power, except for the hanger bags 18, which are battery operated and are operatively connected to the system through infrared (IR) communications or other wireless means.

By way of a non-limiting example, the transmitter 12 may be of the type provided by Global Cache, Model no. GC-CGX, and the connector block 14 may be of the type sold by Xantech, Corp, Model no. CB-12. An example of a suitable IR emitter 16 is sold by Xantech Corporation, entitled BLAST-IR HIDDEN LINK IR BLASTER, Model no. 39020.

Multiple computer work stations 10 may be connected to a server, forming a network. When a pharmacy worker receives an order to fill or refill a prescription, the worker enters the patient and prescription medication information into the computer work station 10 or network (or locates the information previously entered for that particular customer). The prescription may be in written prescription form, a renewable prescription label, or any other tangible medium documenting a request for prescription by a health care provider. The pharmacy worker then reviews the prescription order to determine whether the prescribed medication is in stock, and further determines whether insurance is available to cover the cost of the medication. This review may be computerized, as well.

After the review is complete, the prescription is processed, so that the proper pills are counted and placed into a container, and a bar coded label is applied to the container. Then, the prescription is placed into a hanger bag, and the barcode for the bag is scanned into the system and coupled or linked together with the specific prescription information within the system, so that the prescription is matched with the specific bag within the system. Next, the hanger bag is placed on the will call rack. Although the will call rack may be divided into sections, alphabetically by customer last name, for instance, it is not necessary to divide the rack in any particular manner to facilitate finding the location of the specific bag, because the system is designed to wirelessly activate the transducer (preferably the LED lights 26) located on that specific hanger bag 18 containing the filled prescription.

In one preferred embodiment, each pharmacy worker is assigned a security card that is specific to that particular worker, and is used to identify that worker within the computer system. When a prescription is filled, a pharmacy worker may scan his or her security card, so that the system records which worker filled the prescription, along with a time and date of the transaction. Similarly, when the customer arrives at the pharmacy to pick up the prescription, the pharmacy worker who retrieves the prescription may scan his or her security card in order to match that particular pharmacy worker with the prescription pick-up transaction. In this way, the system records which worker retrieved a specific prescription, and records the time and date of the transaction, along with any other relevant information, as desired. After scanning the security card into the system for a prescription pick-up transaction for a customer, the pharmacy worker then accesses the computer system and selects the appropriate customer record for the prescription to be picked up. When the appropriate customer record for that specific prescription is accessed, the pharmacy worker enters a command for the system to locate the prescription, which is positioned within the hanger bag that is hanging on the will call rack. It should be understood that other, alternative security protocols may be used to identify which pharmacy worker was involved in the filling or the retrieval of the prescription medication. Such alternative security protocols may include assigning pharmacy workers unique user identification codes and passwords, the use of biometric identifying means (retina scanners, fingerprint scanners, and the like), or any other suitable security protocols.

Functionally, as shown in FIG. 1, the computer system sends the command signal to the transmitter 12, which then transmits the signal through the connector block 14, in order to boost the signal strength. The command signal is then received by the infrared (IR) emitter 16, which broadcasts the signal wirelessly to all of the hangers 20 on the will call rack. The computer system is preferably connected to the transmitter 12, connector block 14 and the IR emitter 16 by using cords, and the IR emitter 16 is preferably positioned in relatively close proximity to the will call rack. Each hanger 20 includes an IR receiver 24 and a transducer (LED lights 26), as well as a barcode and a memory chip that is encoded to match the barcode. The electronic components within the hanger 20 may be battery powered. The transducer may be any type of component that may alert the worker, particularly through audio or visual means, to the location of the specific hanger bag being requested. In a preferred embodiment, the transducer includes at least two LED lights 26, one red and one green. When the system sends a signal out through the IR emitter 16, the signal is coded to activate only the specific hanger bag 18 that has been requested, and at least one of the LED lights 26 becomes illuminated, or may flash, in order to alert the pharmacy worker to the location of the hanger bag 18 containing the prescription.

The LED lights 26 may be programmed so that if there are two pharmacy workers, the green light is assigned to one worker and the red light is assigned to the other. In this way, a pharmacy worker using the will call system need only look for the light color assigned to him (red, for instance), while disregarding the green light(s) that were assigned to another worker. Multiple colored lights may be employed for multiple workers. Alternatively, the LED lights 26 may be programmed to emit a specific flashing sequence for a particular worker. It is contemplated that the transducer or LED lights 26 may be programmed in any desired manner to indicate hanger bags 18 specific to a pharmacy worker. The LED lights 26 may also be programmed to indicate when battery power is getting low.

Once the pharmacy worker has identified and located the hanger bag 18 with the requested prescription, the worker then scans the barcode on the hanger 20 and/or the prescription label into the computer system, so that the computer system may compare the requested prescription with the prescription retrieved by the worker in order to ensure that the correct prescription was retrieved for that customer. When the prescription is delivered to the customer, the system generates a receipt, which is then signed by the customer, preferably using an electronic signature pad so that the signature is recorded into the system and linked to the transaction.

It should be understood that other types of components may be used or substituted for components described herein. For instance, the wireless communications between the hanger bag 18 and the computer system may include RFID technology or other electromagnetic wireless communication technology, rather than infrared communication components. Speakers may be used as transducers to emit an audio signal, either instead of or along with LED lights 26. In some cases, a connector block 14 may not be necessary to boost the signal strength of the coded signal.

Although the present invention has been described in considerable detail with reference to certain preferred versions thereof, other versions are possible. Therefore, the spirit and scope of the appended claims should not be limited to the description of the preferred versions contained herein. All features disclosed in this specification may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A method for tracking and locating prescription medications within a pharmacy, said method comprising the steps of:
    receiving a customer order to fill or refill a medical prescription;
    processing said prescription order, including locating a medication specified in said customer order, counting a proper number of doses of said medication, placing said proper number of doses of said medication into a container, and providing a label to be applied to said container;
    providing at least one computer connected to a transmitter for transmitting coded signals;
    establishing on said computer a customer record or accessing an existing customer record;
    establishing a security protocol on said computer to identify a specific pharmacy worker, and identifying and recording information relating to transactions conducted by said pharmacy worker;
    providing a hanger bag, said hanger bag including a hanger, a bag, a bar code, means for receiving said coded signal from said computer, and a transducer connected to said receiving means, wherein said transducer is activated by said coded signal and emits an audio or visual signal upon activation;
    placing said container with said medication into said hanger bag;
    hanging said hanger bag on a will call rack;
    accessing said computer upon arrival of a customer to pick up said medication;
    commanding said computer to send said coded signal to said hanger bag;
    said hanger bag activating said transducer upon receipt of said coded signal;
    retrieving said hanger bag and said container with said medication; and
    scanning said bar code from said hanger bag and allowing said computer to compare said barcode from said hanger bag with said prescription order to ensure that said customer is receiving correct prescription medication.

2. The method set forth in claim 1, wherein said transducer includes at least one LED light.

3. The method set forth in claim 1, wherein said audio or visual signal is specific to said specific pharmacy worker.

4. The method set forth in claim 1, wherein said transmitter is an infrared (IR) transmitter, and said receiving means is an IR receiver.

5. The method set forth in claim 1, wherein said computer communicates with said hanger bag through wireless transmissions.

6. The method set forth in claim 1, wherein said computer is a workstation connected to a computer network.

7. The method set forth in claim 1, wherein said computer is attached to a connector block.

8. The method set forth in claim 1, further including the step of recording and saving information relating to the date and time that a prescription order is filled.

9. The method set forth in claim 1, further including the step of recording and saving information relating to the date and time that said prescription medication is picked up by a customer.

10. The method set forth in claim 1, wherein establishing said security protocol includes the steps comprising:
    providing a computer readable security card capable of identifying a specific pharmacy worker;

assigning said computer readable security card to a specific pharmacy worker, so that a computer system may identify transactions conducted by said specific pharmacy worker; and scanning said computer readable security card into said computer.

11. The method set forth in claim 10, wherein said computer records information identifying which specific pharmacy worker filled said prescription.

12. The method set forth in claim 10, wherein said computer records information identifying which specific pharmacy worker retrieved said prescription for said customer.

13. The method set forth in claim 1, wherein said computer records information identifying which specific pharmacy worker filled said prescription.

14. The method set forth in claim 1, wherein said computer records information identifying which specific pharmacy worker retrieved said prescription for said customer.

* * * * *